(12) United States Patent
Wang et al.

(10) Patent No.: US 12,065,483 B1
(45) Date of Patent: Aug. 20, 2024

(54) SINGLE DOMAIN ANTIBODIES TO INFLUENZA HEMAGGLUTININ A AND B

(71) Applicant: Zhong Wang, Fremont, CA (US)

(72) Inventors: Zhong Wang, Foster City, CA (US); Andrew Wang, Foster City, CA (US); Thomas Nie, Foster City, CA (US)

(73) Assignee: Zhong Wang, Fremont, CA (US)

( * ) Notice: Subject to any disclaimer, the term of this patent is extended or adjusted under 35 U.S.C. 154(b) by 0 days.

(21) Appl. No.: 18/420,507

(22) Filed: Jan. 23, 2024

(51) Int. Cl.
| | |
|---|---|
| *C07K 16/00* | (2006.01) |
| *A61P 31/14* | (2006.01) |
| *A61P 37/04* | (2006.01) |
| *C07K 16/10* | (2006.01) |
| *C12P 21/08* | (2006.01) |
| *A61K 39/00* | (2006.01) |
| *C07K 1/00* | (2006.01) |

(52) U.S. Cl.
CPC .......... *C07K 16/1018* (2013.01); *A61P 31/14* (2018.01); *A61P 37/04* (2018.01); *A61K 2039/505* (2013.01); *C07K 2317/31* (2013.01); *C07K 2317/565* (2013.01); *C07K 2317/569* (2013.01)

(58) Field of Classification Search
None
See application file for complete search history.

*Primary Examiner* — Chun W Dahle
(74) *Attorney, Agent, or Firm* — Sheppard Mullin Richter & Hampton LLP

(57) ABSTRACT

The present disclosure provides single-domain antibodies having binding specificity to both influenza hemagglutinin A and B and thus being capable of neutralizing both influenza A and B viruses.

10 Claims, No Drawings
Specification includes a Sequence Listing.

SINGLE DOMAIN ANTIBODIES TO INFLUENZA HEMAGGLUTININ A AND B

REFERENCE TO AN ELECTRONIC SEQUENCE LISTING

The content of the electronic sequence listing (379467.xml; Size: 16,842 bytes; and Date of Creation: Jan. 14, 2024) is herein incorporated by reference in its entirety.

BACKGROUND

Seasonal flues, caused by influenza viruses (IV), lead to wide-spread morbidity and mortality. It is estimated that around 10% of the global population is infected annually. IV is a member of the Orthomyxoviridae family of segmented, negative-sense, single-stranded RNA viruses. There are four genera of IVs, A (IVA), B (IVB), C (IVC), and D (IVD). The genomes of IVA and IVB consist of eight RNA segments while the genomes of IVC and IVD consist of seven RNA segments, enveloped by a phospholipid bilayer derived from the host membrane. These segments encode for a variety of structural and non-structural proteins.

In IVA and IVB, two of these structural proteins, hemagglutinin (HA) and neuraminidase (NA), are inserted into the phospholipid bilayer as spikes. HA is responsible for viral attachment, entry, and fusion into host cells, while NA cleaves the cell receptor to facilitate viral release.

Vaccines remain the main approach for influenza prevention, but their efficacy is generally low and unpredictable. Moreover, the elderly tends to have reduced reaction to vaccines. Annual selection of vaccine strains presents many challenges and a poor match with circulating viruses can result in undesirable effectiveness. Moreover, most vaccine-induced antibodies are strain-specific.

However, broadly neutralizing antibodies targeting the influenza HA protein have been entered clinical trials as therapeutic agents, but their use in influenza prevention is limited given their inability to target both influenza A and B viruses. Antibody cocktails that include both antibodies specific to the HA of influenza A and B require multiple, high-dose injections throughout the entire influenza season.

SUMMARY

The present disclosure provides single-domain antibodies having binding specificity to both influenza hemagglutinin A and B and thus being capable of neutralizing both influenza A and B viruses. The antibodies, as well as fusion proteins that contain an antibody and other domains such as IgG Fc, or polynucleotide(s) encoding them, can be readily used for the prevention and treatment of influenza A or B infection.

One embodiment of the present disclosure provides a single domain antibody or a polypeptide comprising the single domain antibody, wherein the single domain antibody has binding specificity to influenza hemagglutinin A and B, and comprises a complementarity determining region 1 (CDR1), a CDR2 and a CDR3, wherein the CDR1, CDR2 and CDR3 comprise, respectively, (a) the amino acid sequences of SEQ ID NO:6, 7 and 8; (b) the amino acid sequences of SEQ ID NO:9, 10 and 11; (c) the amino acid sequences of SEQ ID NO:12, 13 and 14; or (d) the amino acid sequences of SEQ ID NO:15, 16 and 17.

In some embodiments, the CDR1 comprises the amino acid sequence of SEQ ID NO:6, the CDR2 comprises the amino acid sequence of SEQ ID NO:7, and the CDR3 comprises the amino acid sequence of SEQ ID NO:8. In some embodiments, the antibody or polypeptide comprises the amino acid sequence of SEQ ID NO:1.

In some embodiments, the CDR1 comprises the amino acid sequence of SEQ ID NO:9, the CDR2 comprises the amino acid sequence of SEQ ID NO:10, and the CDR3 comprises the amino acid sequence of SEQ ID NO: 11. In some embodiments, the antibody or polypeptide comprises the amino acid sequence of SEQ ID NO:2.

In some embodiments, the CDR1 comprises the amino acid sequence of SEQ ID NO:12, the CDR2 comprises the amino acid sequence of SEQ ID NO:13, and the CDR3 comprises the amino acid sequence of SEQ ID NO:14. In some embodiments, the antibody or polypeptide comprises the amino acid sequence of SEQ ID NO:3.

In some embodiments, the CDR1 comprises the amino acid sequence of SEQ ID NO:15, the CDR2 comprises the amino acid sequence of SEQ ID NO:16, and the CDR3 comprises the amino acid sequence of SEQ ID NO:17. In some embodiments, the antibody or polypeptide comprises the amino acid sequence of SEQ ID NO:4.

In some embodiments, the polypeptide comprises two or more of the single domain antibodies. In some embodiments, the polypeptide further comprises a dimerization domain, such as an IgG Fc, or a trimerization domain.

Also provided are polynucleotide(s) encoding the antibody or polypeptide of the present disclosure.

Still further provided, in one embodiment, is a method for preventing or treating infection by an influenza A or B virus, comprising administering to a subject the antibody or polypeptide of the present disclosure, or one or more polynucleotide(s) encoding the antibody or polypeptide. In some embodiments, the administration is intranasal or intravenous.

DETAILED DESCRIPTION

In order that the present disclosure may be more readily understood, certain terms are first defined. Additional definitions are set forth throughout the detailed description.

The term "antibody" as referred to herein includes whole antibodies and any antigen binding fragment (i.e., "antigen-binding portion") or single chains thereof. Whole antibodies are glycoproteins comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, $C_H1$, $C_H2$, and $C_H3$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy terminus in the following order: FR1, CDR1, FR2, CDR2, FR3, CDR3, and FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "antigen-binding portion" of an antibody (or simply "antibody portion" or "fragment"), as used herein, refers to one or more fragments of an antibody that retain the ability to specifically bind to an antigen (e.g., a LAG-3 protein). It has been shown that the antigen-binding function of an antibody can be performed by fragments of a full-length antibody. Examples of binding fragments encompassed within the term "antigen binding portion" of an antibody include (i) a Fab fragment, a monovalent fragment consisting of the $V_L$, $V_H$, $C_L$ and $C_H1$ domains; (ii) a F(ab')$_2$ fragment, a bivalent fragment comprising two Fab fragments linked by a disulfide bridge at the hinge region; (iii) a Fab' fragment, which is essentially a Fab with part of the hinge region (see, FUNDAMENTAL IMMUNOLOGY (Paul ed., 3.sup.rd ed. 1993); (iv) a Fd fragment consisting of the $V_H$ and $C_H1$ domains; (v) a $F_v$ fragment consisting of the $V_L$ and $V_H$ domains of a single arm of an antibody, (vi) a dAb fragment (Ward et al., (1989) Nature 341:544-546), which consists of a $V_H$ domain; (vii) an isolated complementarity determining region (CDR); and (viii) a simple domain antibody, a heavy chain variable region containing a single variable domain and two constant domains. Furthermore, although the two domains of the $F_v$ fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain $F_v$ (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen binding portion" of an antibody. These antibody fragments are obtained using conventional techniques known to those with skill in the art, and the fragments are screened for utility in the same manner as are intact antibodies.

The terms "monoclonal antibody" or "monoclonal antibody composition" as used herein refer to a preparation of antibody molecules of single molecular composition. A monoclonal antibody composition displays a single binding specificity and affinity for a particular epitope.

As used herein, an antibody that "specifically binds the influenza hemagglutinin protein" or "has specificity to the influenza hemagglutinin protein" is intended to refer to an antibody that binds to the influenza hemagglutinin protein but does not substantially bind to non-influenza hemagglutinin proteins. Preferably, the antibody binds to an influenza hemagglutinin protein with "high affinity", namely with a $K_D$ of $1 \times 10^{-7}$ M or less, more preferably $5 \times 10^{-8}$ M or less, more preferably $3 \times 10^{-8}$ M or less, more preferably $1 \times 10^{-8}$ M or less, more preferably $3 \times 10^{-9}$ M or less or even more preferably $1 \times 10^{-9}$ M or less.

The phrases "an antibody recognizing an antigen" and "an antibody specific for an antigen" are used interchangeably herein with the term "an antibody which binds specifically to an antigen."

Various aspects of the disclosure are described in further detail in the following subsections.

As used herein, the terms "treat" or "treatment" refer to both therapeutic treatment and prophylactic or preventative measures, wherein the object is to prevent or slow down (lessen) an undesired physiological change or disorder, such as the progression of cancer.

Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on.

As used herein, phrases such as "to a patient in need of treatment" or "a subject in need of treatment" includes subjects, such as mammalian subjects, that would benefit from administration of an antibody or composition of the present disclosure used, e.g., for detection, for a diagnostic procedure and/or for treatment.

Antibodies Against Hemagglutinin A and B

The present disclosure describes the identification of single domain antibodies capable of binding to the hemagglutinin (HA) protein of both influenza A and B viruses. As demonstrated in the accompanying experimental examples, these antibodies have excellent binding affinity to the HA protein of both types.

Accordingly, in one embodiment of the present disclosure, provided is a single domain antibody or a polypeptide that includes the single domain antibody, wherein the single domain antibody includes a CDR1, a CDR2 and a CDR3, which respectively have the CDR1, CDR2 and CDR3 sequences of any one of the antibodies in Table 3. Some of these CDR sequences (Kabat numbering) are presented in Table 4.

In some embodiments, the CDR1, CDR2, and CDR3 are those of antibody F1-04 (SEQ ID NO:1). In some embodiments, the CDR1, CDR2 and CDR3 include the amino acid sequences of SEQ ID NO:6, 7 and 8, respectively. In some embodiments, the antibody includes the recited CDR1, CDR2 and CDR3 and has at least 80%, 85%, 90%, 95%, 98%, or 99% sequence identity to SEQ ID NO:1.

In some embodiments, the CDR1, CDR2, and CDR3 are those of antibody F2-02 (SEQ ID NO:2). In some embodiments, the CDR1, CDR2 and CDR3 include the amino acid sequences of SEQ ID NO:9, 10 and 11, respectively. In some embodiments, the antibody includes the recited CDR1, CDR2 and CDR3 and has at least 80%, 85%, 90%, 95%, 98%, or 99% sequence identity to SEQ ID NO:2.

In some embodiments, the CDR1, CDR2, and CDR3 are those of antibody F2-20 (SEQ ID NO:3). In some embodiments, the CDR1, CDR2 and CDR3 include the amino acid sequences of SEQ ID NO:12, 13 and 14, respectively. In some embodiments, the antibody includes the recited CDR1, CDR2 and CDR3 and has at least 80%, 85%, 90%, 95%, 98%, or 99% sequence identity to SEQ ID NO:3.

In some embodiments, the CDR1, CDR2, and CDR3 are those of antibody F2-24 (SEQ ID NO:4). In some embodiments, the CDR1, CDR2 and CDR3 include the amino acid sequences of SEQ ID NO:15, 16 and 17, respectively. In some embodiments, the antibody includes the recited CDR1, CDR2 and CDR3 and has at least 80%, 85%, 90%, 95%, 98%, or 99% sequence identity to SEQ ID NO:4.

Also provided, in some embodiments, are anti-hemagglutinin antibodies and antigen binding fragments that compete with any of the antibodies disclosed herein in binding to both human hemagglutinin A and B. Also provided, in some embodiments, are anti-hemagglutinin antibodies and antigen binding fragments that bind to the same epitope as any of the antibodies disclosed herein. Also provided, in some embodiments, are anti-hemagglutinin antibodies and antigen binding fragments that included the CDR1, CDR2, and CDR3 of the antibodies disclosed herein.

Also provided are compositions that include the antibody or the polypeptide and a pharmaceutically acceptable carrier.

It will also be understood by one of ordinary skill in the art that antibodies as disclosed herein may be modified such that they vary in amino acid sequence from the naturally occurring binding polypeptide from which they were derived. For example, a polypeptide or amino acid sequence derived from a designated protein may be similar, e.g., have a certain percent identity to the starting sequence, e.g., it may be 60%, 70%, 75%, 80%, 85%, 90%, 95%, 98%, or 99% identical to the starting sequence. In some embodiments, the modified antibody or fragment retains the designate CDR sequences.

In certain embodiments, the antibody comprises an amino acid sequence or one or more moieties not normally associated with an antibody. Exemplary modifications are described in more detail below. For example, an antibody of the disclosure may comprise a flexible linker sequence, or may be modified to add a functional moiety (e.g., PEG, a drug, a toxin, or a label).

Also provided are bispecific and multispecific antibodies that includes one, two, three or four units of the single domain anti-hemagglutinin antibody as disclosed herein, and one or more other specificities (not hemagglutinin).

The CDR regions recited in this disclosure can also be changed to each of its biological variants. A biological variant of CDR sequence is derived from the original sequence by one, two or three amino acid addition, deletion and/or substitutions. In some embodiments, the substitution is conservative amino acid substitution.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Fusion, Multi-Domain, Dimeric and Trimeric Antibodies

The single domain antibodies of the present disclosure can be fused with other proteins or domains which are contemplated to increase the stability, half-life, affinity, binding diversity or activity of the antibodies. In one example, one, two or more of the same single domain antibodies can be fused to an IgG Fc fragment, which would dimerize. Having multiple copies of the single domain antibodies in a protein can increase the binding.

In some embodiments, one of the single domain antibodies of the present disclosure can be fused with another anti-HA antibody to form a fusion protein. Given their different binding specificity, such a fusion can improve the binding diversity.

In some embodiments, one, two or more of the antibodies of the present disclosure can be fused to a trimerization domain which would trimerize to form a trimer antibody. A trimerization domain is a peptide sequence that is capable of mediating stable association of a trimeric molecule. Trimerization domains are known in the art, such as the domains in trimeric proteins responsible for mediating association of the trimeric protein.

Example trimerization domains include the T4 bacteriophage fibritin trimerization motif (T4F), the GCN4 trimeric leucine zipper motif (GCN4), and the human collagen XVIII derived homotrimerization domain (TIE).

In some embodiments, the fusion protein further includes a peptide linker between the antibody or antigen binding fragment and the trimerization domain. In some embodiments, the peptide linker is flexible. In some embodiments, the distance between antibody the trimerization domain is not longer than 100 amino acids, or not longer than 90, 80, 70, 60, 50, 40, 30, 25, 20, 15 or 10 amino acids. In some embodiments, the peptide linker is from 5 to 50 amino acid residues in length, preferably from 5 to 20 amino acid residues in length.

In another aspect, the present disclosure provides a pharmaceutical composition comprising an antibody of the present disclosure formulated together with a pharmaceutically acceptable earlier. It may optionally contain one or more additional pharmaceutically active ingredients, such as another antibody or a drug. The pharmaceutical compositions of the disclosure also can be administered in a combination therapy with, for example, an anti-viral agent, or a vaccine.

The pharmaceutical composition can comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., Remington: *The Science and Practice of Pharmacy,* 20th Ed. (Lippincott Williams & Wilkins 2003), the disclosure of which is incorporated herein by reference. Preferably, a pharmaceutical composition is suitable for intravenous, intramuscular, subcutaneous, parenteral, spinal or epidermal administration (e.g., by injection or infusion). Depending on the route of administration, the active compound can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrastemal injection and infusion. Alternatively, an antibody of the disclosure can be administered via a non-parenteral route, such as a topical, epidermal or mucosal route of administration, e.g., intranasally, orally, vaginally, rectally, sublingually or topically.

Pharmaceutical compositions can be in the form of sterile aqueous solutions or dispersions. They can also be formulated in a microemulsion, liposome, or other ordered structure suitable to high drug concentration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about ninety-nine percent of active ingredient, preferably from about 0.1% to about 70%, most preferably from about 1% to about 30% of active ingredient in combination with a pharmaceutically acceptable carrier.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. Alternatively, antibody can be administered as a sustained release formulation, in which case less frequent administration is required.

For administration of the antibody, the dosage ranges from about 0.0001 to 100 mg/kg, and more usually 0.01 to 5 mg/kg, of the host body weight. For example, dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every 3 to 6 months. Preferred dosage regimens for an antibody of the disclosure include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks. In some methods, dosage is adjusted to achieve a plasma antibody concentration of about 1-1000 μg/mL and in some methods about 25-300 μg/mL.

A "therapeutically effective dosage" of an antibody of the disclosure preferably results in a decrease in severity of disease symptoms, an increase infrequency and duration of disease symptom-free periods, or a prevention of impairment or disability due to the disease affliction. For example, for the treatment of tumor bearing subjects, a "therapeutically effective dosage" preferably inhibits tumor growth by at least about 20%, more preferably by at least about 40%, even more preferably by at least about 60%, and still more preferably by at least about 80% relative to untreated subjects. A therapeutically effective amount of a therapeutic compound can decrease tumor size, or otherwise ameliorate symptoms in a subject, which is typically a human or can be another mammal.

Polynucleotides, mRNA, and Methods of Expressing or Preparing Antibodies

The present disclosure also provides polynucleotides or nucleic acid molecules encoding the antibodies, variants or derivatives thereof of the disclosure. The polynucleotides of the present disclosure may encode the antibodies, variants or derivatives thereof on the same polynucleotide molecule or on separate polynucleotide molecules.

In some embodiments, the polynucleotide is an mRNA molecule. In some embodiments, the mRNA can be introduced into a target cell for expressing the antibody or fragment thereof.

mRNAs may be synthesized according to any of a variety of known methods. For example, the mRNAs may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor. The exact conditions will vary according to the specific application.

In some embodiments, for the preparation of antibody-coding mRNA, a DNA template is transcribed in vitro. A suitable DNA template typically has a promoter, for example a T3, T7 or SP6 promoter, for in vitro transcription, followed by desired nucleotide sequence for desired antibody encoding mRNA and a termination signal.

Desired antibody encoding mRNA sequence may be determined and incorporated into a DNA template using standard methods. For example, starting from a desired amino acid sequence, a virtual reverse translation is carried out based on the degenerated genetic code. Optimization algorithms may then be used for selection of suitable codons. Typically, the G/C content can be optimized to achieve the highest possible G/C content on one hand, taking into the best possible account the frequency of the tRNAs according to codon usage on the other hand. The optimized RNA sequence can be established and displayed, for example, with the aid of an appropriate display device and compared with the original (wild-type) sequence. A secondary structure can also be analyzed to calculate stabilizing and destabilizing properties or, respectively, regions of the RNA.

The mRNA may be synthesized as unmodified or modified mRNA. Typically, mRNAs are modified to enhance stability. Modifications of mRNA can include, for example, modifications of the nucleotides of the RNA. A modified mRNA can thus include, for example, backbone modifications, sugar modifications or base modifications. In some embodiments, antibody encoding mRNAs may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methyl-thio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, 13-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g. from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosure of which is included here in its full scope by reference.

In some embodiments, the mRNAs may contain RNA backbone modifications. Typically, a backbone modification is a modification in which the phosphates of the backbone of the nucleotides contained in the RNA are modified chemically. Exemplary backbone modifications typically include, but are not limited to, modifications from the group consisting of methylphosphonates, methylphosphoramidates, phosphoramidates, phosphorothioates (e.g., cytidine 5'-O-(1-thiophosphate)), boranophosphates, positively charged guanidinium groups etc., which means by replacing the phosphodiester linkage by other anionic, cationic or neutral groups.

In some embodiments, the mRNAs may contain sugar modifications. A typical sugar modification is a chemical modification of the sugar of the nucleotides it contains including, but not limited to, sugar modifications chosen from the group consisting of 2'-deoxy-2'-fluoro-oligoribonucleotide (2'-fluoro-2'-deoxycytidine 5'-triphosphate, 2'-fluoro-2'-deoxyuridine 5'-triphosphate), 2'-deoxy-2'-deamine-oligoribonucleotide (2'-amino-2'-deoxycytidine 5'-triphosphate, 2'-amino-2'-deoxyuridine 5'-triphosphate), 2'-O-alkyloligoribonucleotide, 2'-deoxy-2'-C-alkyloligoribonucleotide (2'-O-methylcytidine 5'-triphosphate, 2'-methyluridine 5'-triphosphate), 2'-C-alkyloligoribonucleotide, and isomers thereof (2'-aracytidine 5'-triphosphate, 2'-arauridine 5'-triphosphate), or azidotriphosphates (2'-azido-2'-deoxycytidine 5'-triphosphate, 2'-azido-2'-deoxyuridine 5'-triphosphate).

In some embodiments, the mRNAs may contain modifications of the bases of the nucleotides (base modifications). A modified nucleotide which contains a base modification is also called a base-modified nucleotide. Examples of such base-modified nucleotides include, but are not limited to, 2-amino-6-chloropurine riboside 5'-triphosphate, 2-aminoadenosine 5'-triphosphate, 2-thiocytidine 5'-triphosphate, 2-thiouridine 5'-triphosphate, 4-thiouridine 5'-triphosphate, 5-aminoallylcytidine 5'-triphosphate, 5-aminoallyluridine 5'-triphosphate, 5-bromocytidine 5'-triphosphate, 5-bromouridine 5'-triphosphate, 5-iodocytidine 5'-triphosphate, 5-iodouridine 5'-triphosphate, 5-methylcytidine 5'-triphosphate, 5-methyluridine 5'-triphosphate, 6-azacytidine 5'-triphosphate, 6-azauridine 5'-triphosphate, 6-chloropurine riboside 5'-triphosphate, 7-deazaadenosine 5'-triphosphate, 7-deazaguanosine 5'-triphosphate, 8-azaadenosine 5'-triphosphate, 8-azidoadenosine 5'-triphosphate, benzimidazole riboside 5'-triphosphate, N1-methyladenosine 5'-triphosphate, N1-methylguanosine 5'-triphosphate, N6-methyladenosine 5'-triphosphate, 06-methylguanosine 5'-triphosphate, pseudouridine 5'-triphosphate, puromycin 5'-triphosphate or xanthosine 5'-triphosphate.

Typically, mRNA synthesis includes the addition of a "cap" on the N-terminal (5') end, and a "tail" on the C-terminal (3') end. The presence of the cap is important in providing resistance to nucleases found in most eukaryotic cells. The presence of a "tail" serves to protect the mRNA from exonuclease degradation.

Thus, in some embodiments, the mRNAs include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G(5')ppp(5)A and G(5)ppp(5')G.

In some embodiments, the mRNAs include a 3' poly(A) tail structure. A poly-A tail on the 3' terminus of mRNA typically includes about 10 to 300 adenosine nucleotides (e.g., about 10 to 200 adenosine nucleotides, about 10 to 175 adenosine nucleotides, about 10 to 150 adenosine nucleotides, about 10 to 125 adenosine nucleotides, 10 to 100 adenosine nucleotides, about 10 to 75 adenosine nucleotides, about 20 to 70 adenosine nucleotides, or about 20 to 60 adenosine nucleotides). In some embodiments, antibody encoding mRNAs include a 3' poly(C) tail structure. A suitable poly-C tail on the 3' terminus of mRNA typically includes about 10 to 200 cytosine nucleotides (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, the mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length (e.g., about 50 and 400 nucleotides in length, about 50 and 300 nucleotides in length, about 50 and 200 nucleotides in length, or about 50 and 100 nucleotides in length).

In some embodiments, a 5' region of an mRNA includes a sequence encoding a signal peptide, such as those described herein. In particular embodiments, a signal peptide derived from human growth hormone (hGH) is incorporated in the 5' region. Typically, a signal peptide encoding sequence is linked, directly or indirectly, to the heavy chain or light chain encoding sequence at the N-terminus.

In some embodiments, the polynucleotide is provided in a vector, such as a plasmid and a viral vector (e.g., lentiviral and adeno-associated viral (AAV) vectors), The present technology may be used to deliver any antibody known in the art and antibodies that can be produced against desired antigens using standard methods. The present invention may be used to deliver monoclonal antibodies, polyclonal antibodies, antibody mixtures or cocktails, human or humanized antibodies, chimeric antibodies, or bi-specific antibodies.

Uses and Methods

The antibodies, antibody compositions and methods of the present disclosure have numerous in vitro and in vivo utilities involving, for example, detection of an influenza HA protein or preventing or treating influenza viral infection. For example, these molecules can be administered to cells in culture, in vitro or ex vivo, or to human subjects, e.g., in vivo, to enhance immunity in a variety of situations. Accordingly, in one aspect, the disclosure provides a method of modifying an immune response in a subject comprising administering to the subject the antibody, or antigen-binding portion thereof, of the disclosure such that the immune response in the subject is modified. Preferably, the response is enhanced, stimulated or up-regulated.

Preferred subjects include human patients infected with the influenza virus or is at risk of developing influenza infection. In some embodiments, the administration is intranasal, intravenous, intramuscular, or subcutaneous, without limitation.

The disclosure further provides methods for detecting the presence of an influenza virus in a sample, or measuring the amount of the influenza virus, comprising contacting the sample, and a control sample, with an antibody or an antigen binding thereof of the present disclosure, under conditions that allow for formation of a complex between the antibody or portion thereof and the influenza spike protein. The formation of a complex is then detected, wherein a difference complex formation between the sample compared to the control sample is indicative the presence of a influenza virus in the sample. Moreover, the antibodies of the disclosure can be used to purify influenza spike proteins.

Examples

The following examples are included to demonstrate preferred embodiments of the disclosure. It should be appreciated by those of skill in the art that the techniques disclosed in the examples which follow represent techniques discovered by the inventors to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

Example 1. Generation and Testing of Single Domain Antibodies Against Influenza Hemagglutinin A and B This example describes the generation and testing of certain single domain antibodies against both influenza hemagglutinin A and B.

Immunization

Alpaca was immunized with Influenza Hemagglutinin A and B antigens, followed by phage library construction and selection.

Animal Immune Response Testing

Animal (Alpaca) immunization was performed at Antibodies Inc (Davis, CA). To test the immune response, serum samples against the immobilized immunogens was analyzed by ELISA. The sera after 5th immunization were evaluated. The antigens were diluted in coating buffer at 1 μg/ml, respectively. The microtiter plate was coated with diluted antigen at 4° C. overnight. The plates were then washed with washing buffer for 3 times before being blocked with blocking buffer at 37° C. for 2 hours. The plates were washed again with washing buffer for 4 times. A series of diluted sera was added to the plates, incubated at 37° C. for 2 hours. Then the plates were washed with washing buffer for 4 times. Goat anti-llama IgG [HRP] secondary antibody was added to the plate and incubated at 37° C. for 1 hour. After washing, the reaction was developed with TMB substrate for 10 minutes and stopped by 1 M HCl. The absorbance of each well at 630 nm was measured using Molecular Dynamics spectrometer.

ELISA Testing of Alpaca Sera

Elisa testing of the alpaca sera also employed a reference multi-domain VHH antibody (VHH-Fc) from Laursen et al., Science. 2018 Nov. 2; 362(6414):598-602 (SEQ ID NO:7). The plates were coated with Influenza A Hemagglutinin at 1 μg/ml on a 96-well Elisa plate. The control VHH antibody was added at 1:3 dilution beginning at 30 μg/ml, and alpaca serum was added with duplicates from 1:3 dilutions. The control VHH antibody was detected with anti-human Fc HRP and Alpaca serum with goat anti-llama VHH HRP. The results are shown in Table 1.

TABLE 1

ELISA Testing with Control VHH

| Control VHH | Alpaca serum | Alpaca serum |
|---|---|---|
| 1.2763 | 0.9556 | 0.6787 |
| 1.2213 | 1.3013 | 1.2491 |
| 1.0856 | 1.2449 | 1.1789 |
| 0.8872 | 0.9721 | 0.8603 |
| 0.5617 | 0.6178 | 0.4994 |
| 0.3215 | 0.3605 | 0.2931 |
| 0.1986 | 0.2048 | 0.1576 |
| 0.1312 | 0.1223 | 0.1076 |

Phage Library Construction and Screening

After immunization, 150 ml-200 ml blood was drawn from each animal. Then the PBMC was isolated. Total RNA was extracted from the isolated lymphocytes according to the manual of RNeasy RNA purification kit from Qiagen. The quantity and quality of total RNA was measured by OD 260/280 and 260/230.

Total RNA was reverse-transcribed into cDNA using oligo(dT)20 primer according to the manual of the SuperScript IV 1st Strand cDNA Synthesis Kit from Thermo Scientific.

Two forward and two reverse specific degenerate primers were designed for the amplification of $V_H$H fragments. The $V_H$H fragment was amplified according to standard PCR operating procedure.

The $V_H$H PCR products were obtained by amplification using different primer pairs. The PCR products were gel purified. The gel purified fragments were assembled into phagemid vector using NEBuilder HiFi assembly master mix. Assembled library was electropoated into SS320 competent cells. Transformants were recovered at 37C for 1 hour, followed by infection with K07 helper phages for another hour. Add more 2×YT media and 100 ug/mL ampicillin and 50 μg/mL Kanamycin to continue culture overnight at 30° C. in an incubator shaker. At the same time 10 μl of the transformed cells were 10-fold serial diluted and plated on 2×YT plates supplemented with 100 μg/ml ampicillin. The colonies were counted to calculate the library size. Positive clones were randomly picked and sequenced to assess the quality of the library.

Next day, 20% PEG/2.5M NaCl was used to precipitate phage library. Purified phage libraries were stored in 50% glycerol at −20° C.

Phase screening was conducted as follows. The antigens were coated onto ELISA microtiter plates, which were blocked with the SuperBlock buffer. One OD/mL phage library was added into ELISA plate, and was incubated for 2 hour at room temperature. The plates were washed with PBST (pH 7.4) 10-15 times. The samples were eluted with 50 mM HCl, and neutralized with 1 mM Tris pH 8.0. The phages were allowed to infect exponential growth XL-blue with and were eluted for 1 hour. M3KO7 helper phage was added and incubated for 1 hour. Carbenicillin and kanamycin were then added into culture media. The selection was repeated for additional 1-2 time until there was clear enrichment.

Recombinant VHH Antibody Expression and Testing

Transient transfection of 293 cells were conducted with miniprep plasmid DNA. Briefly, 1 µg of DNA was mixed with lipid transfection reagent, and DNA/lipid mix was incubated at room temperature for 20 min, then the mix was added into 1 mL 293 suspension culture for 3-5 days. At the end of the culture, supernatants were collected and stored at 4° C.

The example then used phages screened with Influenza Hemagglutinin A and B, Influenza Hemagglutinin A only, or Influenza Hemagglutinin B only (1 μg/mL) to do ELISA to test the selected clones. In total, four unique $V_H$H against both Influenza Hemagglutinin A and Influenza Hemagglutinin B were obtained. The testing data are shown in Table 2, and relevant sequences are provided in Table 3.

TABLE 2

ELISA Testing Results of Selected Antibodies

| | F1-04 | F2-02 | F2-20 | F2-24 |
|---|---|---|---|---|
| Influenza Hemagglutinin A (nM) | | | | |
| Supernatants | | | | |
| 1:10 | 1.762 | 1.211 | 0.884 | 0.444 |
| 1:100 | 1.999 | 1.088 | 0.629 | 0.427 |
| 1:1000 | 0.366 | 0.730 | 0.442 | 0.279 |
| 1:10000 | 0.058 | 0.405 | 0.269 | 0.150 |
| Influenza Hemagglutinin B (nM) | | | | |
| Supernatant dilution | | | | |
| 1:10 | 1.466 | 0.826 | 1.577 | 1.691 |
| 1:100 | 1.633 | 0.863 | 1.518 | 1.847 |
| 1:1000 | 0.738 | 0.61 | 1.195 | 1.628 |
| 1:10000 | 0.205 | 0.266 | 0.805 | 1.451 |

TABLE 3

Antibody Sequences

| Antibody | Sequence | SEQ ID NO: |
|---|---|---|
| F1-04 | QVQLVESGGGLVQVGGSLRLSCAASERPSSNYAMGWFRQAPGKEQEFVAAIYWSGGGTAYGDSVKGRFTISKDNAKNTVYLQMNDLKPEDIGMYYCTTDHYGSWSYEYGSWGQGTQVTVSS | 1 |
| F2-02 | QVQLVESGGGLVQAGGSLRLSCAASGRTFRSFAMGWFRQAPGKEREFVATISWWSNNTYYADSVKGRFTISRDIAKNTVYLQMNSLKPEDTAVYYCAADLGPWLTAGQYDYWGQGTQVTVSS | 2 |
| F2-20 | QVQLVESGGGLVQAGGSLRLSCAASGRTFSRYAMGWFRQAPGKEREFVARISWSGDITYYADSVKGRFTISRDNAKNTVYLQMNSLKPEDTAVYYCAADAILRTRPPYESDYWGQGTQVTVSS | 3 |
| F2-24 | QVQLVESGGGLVQAGGSLRLSCASSGHTFNSYVMGWFRQAPGKEREFVAAIRPSGVSTYYADSVKGRFTISRDNAKNTVSLEMNSLKPEDTAVYYCAGDRDHSMMAVRRLSSYRQWGRGTQVTVSS | 4 |
| Control multi-domain VHH-Fc | EVQLVESGGGLVQPGGSLRLSCAVSISIFDIYAMDWYRQAPGKQRDLVATSERDGSTNYADSVKGRFTISRDNAKNTLYLQMNSLKPEDTAVYLCHVSLYRDPLGVAGGMGVYWGKGALVTVSSAAAGGGGSGGGGSGGGGSGGGGSGGGGSGGGGSGGGGSEVQLVESGGGLVQAGGSLKLSCAASGRTYAMGWFRQAPGKEREFVAHINALGTRTYYSDSVKGRFTISRDNAKNTEYLEMNNLKPEDTAVYYCTAQGQWRAAPVAVAAEYEFWGQGTQVTVSAAAGGGGSGGGGSGGGGSGGGGSGGGGSGGGGSGGGGSEVQLVESGGGLVQPGGSLRLSCAATGFTLENKAIGWFRQTPGSEREGVLCISKSGSWTYYTDSMRGRFTISRDNAENTVYLQMDSLKPEDTAVYYCATTTAGGGLCWDGTTFSRLASSWGQGTQVTVSSAAAGGGGSGGGGSGGGGSGGGGSGGGGSGGGGSGGGGSEVQLVESGGGLVQPGGSLRLSCAASGFTFSTSWMYWLRQAPGKGLEWVSVINTDGGTYYADSVKGRFTISRDNSKNTLYLQMNSLRAEDTAVYYCAKDWGGPEPTRGQGTLVTVSSAAAGGGGSGGGGSGGGGSGGGGSGGGGSGGGGSGGGGSASPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK | 5 |

TABLE 4

CDR Sequences

| Antibody | Sequence | SEQ ID NO: |
|---|---|---|
| F1-04 | NYAMG | 6 |
| | AIYWSGGGTAYGDSVKG | 7 |
| | DHYGSWSYEYGS | 8 |
| F2-02 | SFAMG | 9 |
| | TISWWSNNTYYADSVKG | 10 |
| | DLGPWLTAGQYDY | 11 |
| F2-20 | RYAMG | 12 |
| | RISWSGDITYYADSVKG | 13 |
| | DAILRTRPPYESDY | 14 |
| F2-24 | SYVMG | 15 |
| | AIRPSGVSTYYADSVKG | 16 |
| | DRDHSMMAVRRLSSYRQ | 17 |

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

The invention claimed is:

1. A single domain antibody or a polypeptide comprising the single domain antibody, wherein the single domain antibody has binding specificity to influenza hemagglutinin A and B, and comprises a complementarity determining region 1 (CDR1), a CDR2 and a CDR3, wherein the CDR1, CDR2 and CDR3 comprise, respectively,
   (a) the amino acid sequences of SEQ ID NO:6, 7 and 8;
   (b) the amino acid sequences of SEQ ID NO:9, 10 and 11;
   (c) the amino acid sequences of SEQ ID NO:12, 13 and 14; or
   (d) the amino acid sequences of SEQ ID NO:15, 16 and 17.

2. The antibody or polypeptide of claim 1, wherein the CDR1 comprises the amino acid sequence of SEQ ID NO:6, the CDR2 comprises the amino acid sequence of SEQ ID NO:7, and the CDR3 comprises the amino acid sequence of SEQ ID NO:8.

3. The antibody or polypeptide of claim 2, which comprises the amino acid sequence of SEQ ID NO:1.

4. The antibody or polypeptide of claim 1, wherein the CDR1 comprises the amino acid sequence of SEQ ID NO:9, the CDR2 comprises the amino acid sequence of SEQ ID NO:10, and the CDR3 comprises the amino acid sequence of SEQ ID NO:11.

5. The antibody or polypeptide of claim 2, which comprises the amino acid sequence of SEQ ID NO:2.

6. The antibody or polypeptide of claim 1, wherein the CDR1 comprises the amino acid sequence of SEQ ID NO:12, the CDR2 comprises the amino acid sequence of SEQ ID NO:13, and the CDR3 comprises the amino acid sequence of SEQ ID NO:14.

7. The antibody or polypeptide of claim 6, which comprises the amino acid sequence of SEQ ID NO:3.

8. The antibody or polypeptide of claim 1, wherein the CDR1 comprises the amino acid sequence of SEQ ID NO:15, the CDR2 comprises the amino acid sequence of SEQ ID NO:16, and the CDR3 comprises the amino acid sequence of SEQ ID NO:17.

9. The antibody or polypeptide of claim 8, which comprises the amino acid sequence of SEQ ID NO:4.

10. The antibody or polypeptide of claim 1, wherein the polypeptide comprises two or more of the single domain antibodies.

* * * * *

SEQUENCE LISTING

```
Sequence total quantity: 17
SEQ ID NO: 1            moltype = AA  length = 121
FEATURE                 Location/Qualifiers
source                  1..121
                        mol_type = protein
                        organism = synthetic construct
SEQUENCE: 1
QVQLVESGGG LVQVGGSLRL SCAASERPSS NYAMGWFRQA PGKEQEFVAA IYWSGGGTAY    60
GDSVKGRFTI SKDNAKNTVY LQMNDLKPED TGMYYCTTDH YGSWSYEYGS WGQGTQVTVS   120
S                                                                  121

SEQ ID NO: 2            moltype = AA  length = 122
FEATURE                 Location/Qualifiers
source                  1..122
                        mol_type = protein
                        organism = synthetic construct
SEQUENCE: 2
QVQLVESGGG LVQAGGSLRL SCAASGRTFR SFAMGWFRQA PGKEREFVAT ISWWSNNTYY    60
ADSVKGRFTI SRDIAKNTVY LQMNSLKPED TAVYYCAADL GPWLTAGQYD YWGQGTQVTV   120
SS                                                                 122

SEQ ID NO: 3            moltype = AA  length = 123
FEATURE                 Location/Qualifiers
source                  1..123
                        mol_type = protein
                        organism = synthetic construct
SEQUENCE: 3
QVQLVESGGG LVQAGGSLRL SCAASGRTFS RYAMGWFRQA PGKEREFVAR ISWSGDITYY    60
ADSVKGRFTI SRDNAKNTVY LQMNSLKPED TAVYYCAADA ILRTRPPYES DYWGQGTQVT   120
VSS                                                                123

SEQ ID NO: 4            moltype = AA  length = 126
FEATURE                 Location/Qualifiers
source                  1..126
                        mol_type = protein
                        organism = synthetic construct
SEQUENCE: 4
QVQLVESGGG LVQAGGSLRL SCASSGHTFN SYVMGWFRQA PGKEREFVAA IRPSGVSTYY    60
ADSVKGRFTI SRDNAKNTVS LEMNSLKPED TAVYYCAGDR DHSMMAVRRL SSYRQWGRGT   120
QVTVSS                                                             126

SEQ ID NO: 5            moltype = AA  length = 876
FEATURE                 Location/Qualifiers
source                  1..876
                        mol_type = protein
                        organism = synthetic construct
SEQUENCE: 5
EVQLVESGGG LVQPGGSLRL SCAVSISIFD IYAMDWYRQA PGKQRDLVAT SFRDGSTNYA    60
DSVKGRFTIS RDNAKNTLYL QMNSLKPEDT AVYLCHVSLY RDPLGVAGGM GVYWGKGALV   120
TVSSAAAGGG GSGGGGSGGG GSGGGGSGGG GSGGGGSGGG GSEVQLVESG GGLVQAGGSL   180
KLSCAASGRT YAMGWFRQAP GKEREFVAHI NALGTRTYYS DSVKGRFTIS RDNAKNTEYL   240
EMNNLKPEDT AVYYCTAQGQ WRAAPVAVAA EYEFWGQGTQ VTVSAAGGG GSGGGGSGGG    300
GSGGGGSGGG GSGGGGSGGG GSEVQLVESG GGLVQPGGSL RLSCAATGFT LENKAIGWFR   360
```

-continued

```
QTPGSEREGV LCISKSGSWT YYTDSMRGRF TISRDNAENT VYLQMDSLKP EDTAVYYCAT  420
TTAGGGLCWD GTTFSRLASS WGQGTQVTVS SAAAGGGGSG GGGSGGGGSG GGGSGGGGSG  480
GGGSGGGGSE VQLVESGGGL VQPGGSLRLS CAASGFTFST SWMYWLRQAP GKGLEWVSVI  540
NTDGGTYYAD SVKGRFTISR DNSKNTLYLQ MNSLRAEDTA VYYCAKDWGG PEPTRGQGTL  600
VTVSSAAGG GGSGGGGSGG GGSGGGGSGG GGSGGGGSGG GGSASPKSCD KTHTCPPCPA  660
PELLGGPSVF LFPPKPKDTL MISRTPEVTC VVVDVSHEDP EVKFNWYVDG VEVHNAKTKP  720
REEQYNSTYR VVSVLTVLHQ DWLNGKEYKC KVSNKALPAP IEKTISKAKG QPREPQVYTL  780
PPSREEMTKN QVSLTCLVKG FYPSDIAVEW ESNGQPENNY KTTPPVLDSD GSFFLYSKLT  840
VDKSRWQQGN VFSCSVMHEA LHNHYTQKSL SLSPGK                            876

SEQ ID NO: 6              moltype = AA   length = 5
FEATURE                   Location/Qualifiers
source                    1..5
                          mol_type = protein
                          organism = synthetic construct
SEQUENCE: 6
NYAMG                                                                5

SEQ ID NO: 7              moltype = AA   length = 17
FEATURE                   Location/Qualifiers
source                    1..17
                          mol_type = protein
                          organism = synthetic construct
SEQUENCE: 7
AIYWSGGGTA YGDSVKG                                                  17

SEQ ID NO: 8              moltype = AA   length = 12
FEATURE                   Location/Qualifiers
source                    1..12
                          mol_type = protein
                          organism = synthetic construct
SEQUENCE: 8
DHYGSWSYEY GS                                                       12

SEQ ID NO: 9              moltype = AA   length = 5
FEATURE                   Location/Qualifiers
source                    1..5
                          mol_type = protein
                          organism = synthetic construct
SEQUENCE: 9
SFAMG                                                                5

SEQ ID NO: 10             moltype = AA   length = 17
FEATURE                   Location/Qualifiers
source                    1..17
                          mol_type = protein
                          organism = synthetic construct
SEQUENCE: 10
TISWWSNNTY YADSVKG                                                  17

SEQ ID NO: 11             moltype = AA   length = 13
FEATURE                   Location/Qualifiers
source                    1..13
                          mol_type = protein
                          organism = synthetic construct
SEQUENCE: 11
DLGPWLTAGQ YDY                                                      13

SEQ ID NO: 12             moltype = AA   length = 5
FEATURE                   Location/Qualifiers
source                    1..5
                          mol_type = protein
                          organism = synthetic construct
SEQUENCE: 12
RYAMG                                                                5

SEQ ID NO: 13             moltype = AA   length = 17
FEATURE                   Location/Qualifiers
source                    1..17
                          mol_type = protein
                          organism = synthetic construct
SEQUENCE: 13
RISWSGDITY YADSVKG                                                  17

SEQ ID NO: 14             moltype = AA   length = 14
FEATURE                   Location/Qualifiers
source                    1..14
                          mol_type = protein
                          organism = synthetic construct
```

```
SEQUENCE: 14
DAILRTRPPY ESDY                                                              14

SEQ ID NO: 15         moltype = AA  length = 5
FEATURE               Location/Qualifiers
source                1..5
                      mol_type = protein
                      organism = synthetic construct
SEQUENCE: 15
SYVMG                                                                         5

SEQ ID NO: 16         moltype = AA  length = 17
FEATURE               Location/Qualifiers
source                1..17
                      mol_type = protein
                      organism = synthetic construct
SEQUENCE: 16
AIRPSGVSTY YADSVKG                                                           17

SEQ ID NO: 17         moltype = AA  length = 17
FEATURE               Location/Qualifiers
source                1..17
                      mol_type = protein
                      organism = synthetic construct
SEQUENCE: 17
DRDHSMMAVR RLSSYRQ                                                           17
```